United States Patent [19]

Miyoshi et al.

[11] 4,061,650

[45] Dec. 6, 1977

[54] 5-TRIHALOGENOMETHYL-4,5-DIHYRO-OXAZOLE-4-CARBOXYLIC ACID ESTERS

[75] Inventors: Munetsugu Miyoshi, Nishinomiya; Kazuo Matsumoto, Kawanishi; Yuji Urabe; Tameo Iwasaki, both of Itami, all of Japan

[73] Assignee: Tanabe Seiyaku Co., Ltd., Osaka, Japan

[21] Appl. No.: 635,361

[22] Filed: Nov. 26, 1975

[30] Foreign Application Priority Data

Dec. 26, 1974 Japan .................................. 49-619

[51] Int. Cl.$^2$ ........................................... C07D 263/14
[52] U.S. Cl. ............................ 260/307 F; 260/534 M
[58] Field of Search ................................... 260/307 F

[56] References Cited

U.S. PATENT DOCUMENTS

| | | | |
|---|---|---|---|
| 2,446,192 | 8/1948 | Pfister et al. | 260/534 |
| 2,530,627 | 11/1950 | Pfister et al. | 260/471 |
| 2,556,791 | 6/1951 | Billman et al. | 260/534 |

FOREIGN PATENT DOCUMENTS 2,027,612  12/1971  Germany.

OTHER PUBLICATIONS

Matsumoto et al., C.A. 83, 179551u, (1975), Abstract of Agric. Biol. Chem. 1975, 39(a), 1869–1873.
Bretschneider et al., C.A. 50, 305a, (1956), Abstract of Monatsh, 85, 1110–1118, (1954).

Primary Examiner—Raymond V. Rush
Attorney, Agent, or Firm—Bierman & Bierman

[57] ABSTRACT

Alkyl (or aralkyl) α-isocyanoacetate is condensed with a trihalogenoacetic aldehyde or its hydrate in the presence of an amine to give trans-4-alkoxycarbonyl(or aralkyloxycarbonyl)-5-trihalogenomethyl-2-oxazoline. The oxazoline compound is hydrolyzed under acidic conditions to give threo-γ,γ,γ-trihalogenothreonine, which is then subjected to catalytic or electrolytic reduction. The above-mentioned reactions can be carried out stereoselectively and threo-threonine is thereby obtained without by-products such as allo-threonine.

1 Claim, No Drawings

5-TRIHALOGENOMETHYL-4,5-DIHYRO-OXAZOLE-4-CARBOXYLIC ACID ESTERS

This invention relates to a novel process for preparing threo-threonine.

Threo-threonine is the threo-type stereoisomer of α-amino-β-hydroxybutyric acid and is useful as a nutrient source. On the other hand, another stereoisomer of α-amino-β-hydroxybutyric acid, i.e., allo-threonine, has no nutritional value.

Several methods of preparing threonine have been known up to now. For example, it is prepared by the steps of subjecting ethyl α-phenylazoacetoacetate to reductive acetylation, hydrogenating the resultant ethyl α-acetamido-acetoacetate in the presence of a catalyst to give ethyl α-acetamido-β-hydroxybutylate, and hydrolyzing the resultant butyrate with hydrochloric acid [The Journal of the American Chemical Society, volume 71, pages 1101 - 1105 (1949)]. Alternatively, threonine may be prepared by reacting acetoaldehyde with copper glycinate to produce the copper chelate of threonine, and then removing copper ion therefrom [U.S. Pat. No. 2,999,878, Bulletin of the Chemical Society of Japan, volume 30, pages 937 - 938(1957)]. These methods are still disadvantageous in that the reaction products thereof are always obtained as a mixture of threo-threonine and allo-threonine. Further, the former method gives more allo-threonine than threo-threonine. In the latter method, the quantitative ratio of allo-threonine to threo-threonine in the product is about 1 : 1.6 and said ratio can not be increased over 1 : 2.4 even by repeated recrystallization of the product.

The present invention provides a method which can achieve the stereoselective synthesis of threo-threonine. It also provides a method of preparing said amino acid without any by-products such as allo-threonine. It further provides novel intermediates in the synthesis of threo-threonine, and a simple and convenient method of preparing said amino acid through said intermediates. Further objects of the present invention will be apparent from the following descriptions of the invention.

According to the present invention, threo-threonine can be prepared by the steps of (1) condensing alkyl (or aralkyl) α-isocyanoacetate with a trihalogenoacetic aldehyde or its hydrate to produce trans-4-alkoxycarbonyl(or aralkyloxycarbonyl)-5-trihalogenomethyl-2-oxazoline, (2) hydrolyzing the oxazoline compound under acidic conditions to produce threo-γ,γ,γ-trihalogenothreonine, and (3) subjecting the resultant trihalogenothreonine to catalytic hydrogenation or electrolytic reduction. The above-mentioned reactions are shown by the following scheme.

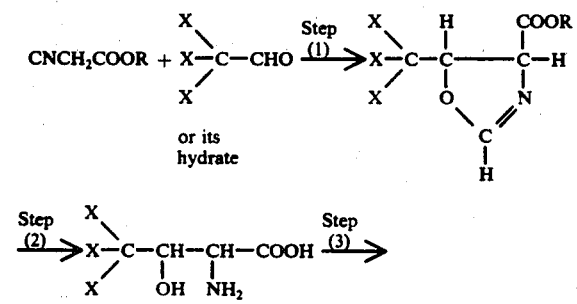

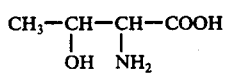

-continued $$CH_3-CH-CH-COOH$$
$$\quad\quad\ |\quad\ |$$
$$\quad\quad OH\ NH_2$$

wherein R is lower alkyl or phenyl-lower alkyl, and X is halogen.

Representative examples of R include methyl, ethyl, propyl, isopropyl, butyl, isobutyl, tert-butyl, amyl, isoamyl and aralkyl such as benzyl. Among these examples of R, alkyl group of one to six carbon atoms is especially suitable for the purpose of the present invention. On the other hand, examples of X include chlorine and bromine.

The condensation reaction of the alkyl (or aralkyl) α-isocyanoacetate with the trihalogenoacetic aldehyde or its hydrate [i.e., Step (1)] can be carried out in a solvent. Alkanols (e.g., methanol, ethanol), tetrahydrofuran, benzene, dimethylformamide and the like are preferably employed as the solvent. It is preferred to carry out the reaction in the presence of an amine at a temperature of −5° to 60° C, especially 5° to 20° C. Suitable examples of the amine include secondary or tertiary organic amines such as di- or tri-lower alkyl amine (e.g., trimethylamine, triethylamine, di-isopropylamine), pyridine and piperidine. By the above-mentioned reaction, trans-4-alkoxycarbonyl (or aralkyloxy-carbonyl)-5-trihalogenomethyl-2-oxazoline is produced stereoselectively without cis-4-alkoxycarbonyl (or aralkyloxycarbony)-5-trihalogenomethyl-2-oxazoline. The product thus obtained may be employed in the subsequent step without isolation from the reaction solution.

The hydrolysis of the oxazoline compound [i.e., Step (2)] can be conducted under acidic conditions in a solvent. For example, said hydrolysis is preferably carried out by the use of a mineral acid. Water and alkanols (e.g., methanol, ethanol) are suitable as the reaction solvent. Hydrochloric acid and sulfuric acid may be employed as the mineral acid. It is preferred to carry out the reaction at a temperature of 10° to 100° C, especially 50° to 90° C.

The hydrogenation of threo-γ,γ,γ-trihalogenothreonine [i.e., Step (3)] can be carried out in a solvent in the presence of a catalyst such as palladium-carbon, Raney nickel or platinum oxide. Water and aqueous alkanols (e.g., aqueous methanol, aqueous ethanol) are suitable as the reaction solvent. It is preferred to carry out the reaction at a temperature of 10° to 150° C, especially 20° to 60° C under atmospheric pressure. Alternatively, threo-threonine can be prepared by electrolytic reduction of threo-γ,γ,γ-trihalogenothreonine. The electrolytic reduction can be accomplished in a conventional manner. For example, it may be carried out in an electrolysis cell which is separated into two chambers by a porous divider. Unglazed ceramics and glass filters are suitable as the porous divider. Suitable examples of the anode materials include platinum, lead, carbon and stainless steel. On the other hand, suitable examples of the cathode materials include mercury, palladium and spongy zinc. In carrying out the electrolysis, a solution of threo-γ,γ,γ-trihalogenothreonine containing a supporting electrolyte is charged into the cathode chamber, and a solution of a supporting electrolyte into the anode chamber. Tetraethylammonium chloride and hydrochloric acid may be employed as the supporting electrolyte. Water and aqueous alkanols (e.g., aqueous methanol, aqueous ethanol) are suitable as the reaction solvent. It is preferred to carry out the reaction at a current density of 20 to 300 mA/cm², especially 50 to 100 mA/cm². It is also preferred to carry it out at a temperature of 0° to 40° C, especially 10° to 25° C.

Threo-threonine produced in the above mentioned Step (3) may be readily purified in a conventional manner, for example, by recrystallization or chromatography on a column of an ion exchange resin. Threo-threonine thus obtained does not contain allothreonine.

Practical and presently-preferred embodiments of the present invention are illustratively shown in the following Examples. Throughout the specification and claims, the term "lower alkyl" should be interpreted as referring to "alkyl of one to six carbon atoms."

EXAMPLE 1

A. 11.4 g of isoproply α-isocyanoacetate and 30 g of triethylamine are dissolved in 100 ml of tetrahydrofuran. 17 g of chloral hydrate are added to the solution at −5° to 0° C. Then, the mixture is stirred at room temperature overnight. The reaction mixture is evaporated under reduced pressure to remove tetrahydrofuran and triethylamine. The residue is extracted with ethyl acetate. The extract is washed with water, dried, and then evaporated under reduced pressure to remove solvent. The residue thus obtained is distilled under reduced pressure, whereby 21.5 of trans-4-isopropoxycarbonyl-5-trichloromethyl-2-oxazoline are obtained. Yield: 87% B.p. 103° C/1 mmHg Infrared absorption spectrum

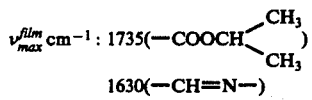

$\nu_{max}^{film}$ cm$^{-1}$: 1735(—COOCH(CH$_3$)$_2$)

1630(—CH=N—)

Nuclear magnetic resonance spectrum

δ(in CDCl$_3$): 1.35(6H, d), 4.77(1H, d, d), 5.14(1H, m), 5.36(1H, d), 7.06(1H, d)

B. 7 g of trans-4-Isopropoxycarbonyl-5-trichloromethyl-2-oxazoline are suspended in 200 ml of 6N-hydrochloric acid. The suspension is stirred at 85° to 90° C for 2 hours. Then, the suspension is concentrated under reduced pressure, and the residue thus obtained is washed with acetone, whereby 6 g of threo-γ,γ,γ-trichlorothreonine hydrochloride are obtained. Yield: 90.8% M.p. 193° − 195° C(decomp.)

Infrared absorption spectrum $\nu_{max}^{nujol}$ cm$^{-1}$: 1730(COOH)

Nuclear magnetic resonance spectrum δ(in d$_6$-DMSO): 4.19(1H, d), 4.68(1H, d), 8.75(5H, broad)

C. 3 g of threo-γ,γ,γ-trichlorothreonine hydrochloride are dissolved in 50 ml of water, and 0.1 g of 10% palladium-carbon is added to the solution. Hydrogen gas is introduced into the mixture at room temperature until hydrogen uptake is completed. The initial pressure of hydrogen gas is adjusted to 50 psi. Then, the catalyst is removed by filtration and the filtrate is concentrated to dryness under reduced pressure. 1.8 g of threo-threonine hydrochloride are obtained. 1.8 g of threo-threonine hydrochloride are dissolved in 10% aqueous ammonia, and the pH of the solution is adjusted to the isoelectric point of threonine. The crystalline precipitate is collected by filtration. 1.28 g of threo-threonine are thereby obtained. Yield: 93% M.p. 184° − 190° C(decomp.) No allo-threonine is observed on the paper chromatogram and IR or NMR-spectrum of the product.

EXAMPLE 2

A. 5.0 g of methyl α-isocyanoacetate and 5.0 g of triethylamine are dissolved in 40 ml of benzene. 7.4 g of chloral are added to the solution at 0° C under stirring. The mixture is stirred at room temperature for 4 hours. Then, the mixture is neutralized with acetic acid, and evaporated under reduced pressure to remove solvent. The residue is dissolved in 50 ml of ethyl acetate. The solution is washed with water, dried, and then evaporated under reduced pressure to remove ethyl acetate. The residue thus obtained is distilled under reduced pressure. 10.6 g of trans-4-methoxycarbonyl-5-trichloromethyl-2-oxazoline are obtained. Yield: 85% B.p. 95° C/1 mmHg Infrared absorption spectrum $\nu_{max}^{nujol}$ cm$^{-1}$: 1745(—COOCH$_3$), 1630(—CH=N—)

Nuclear magnetic resonance spectrum

δ(in CDCl$_3$): 3.89(3H, s), 4.84(1H, d, d), 5.41(1H, d), 7.08(1H, d)

Trans-4-tert-butoxycarbonyl-5-trichloromethyl-2-oxazoline is obtained from tert-butyl α-isocyanoacetate in the same manner as described above. Yield: 95% B.p. 93° C/0.8 mmHg Infrared absorption spectrum $\nu_{max}^{film}$ cm$^{-1}$: 1750(—COOC(CH$_3$)), 1620(—CH=N—)

Nuclear magnetic resonance spectrum

δ(in CDCl$_3$): 1.5(9H, s), 4.74(1H, d, d), 5.35(1H, d), 7.08(1H, d)

B. Trans-4-methoxycarbonyl-5-trichloromethyl-2-oxazoline and trans-4-tert-butoxycarbonyl-5-trichloromethyl-2-oxazoline are respectively treated in the same manner as described in Example 1-(B), whereby threo-γ,γ,γ-trichlorothreonine hydrochloride is obtained. Threo-γ,γ,γ-trichlorothreonine hydrochloride thus obtained is treated in the same manner as described in Example 1-(C), whereby threo-threonine is obtained.

EXAMPLE 3

A. 5.6 g of tert-butyl α-isocyanoacetate and 1.3 g of triethylamine are dissolved in 50 ml of benzene. 5.9 g of chloral are added dropwise to the solution at 5° to 10° C. The solution is stirred at room temperature for 2 hours. The reaction solution is evaporated under reduced pressure to remove benzene and triethylamine. 50 ml of 2N-hydrochloric acid are added to the residue, and the mixture is stirred at 40° to 50° C for 2 hours. Then, the mixture is concentrated under reduced pressure, and the residue thus obtained is dissolved in 30 ml of methanol. The solution is adjusted to pH 6.5 with pyridine. The crystalline precipitate is collected by filtration, and washed with acetone. 8.2 g of threo-γ,γ,γ-trichlorothreonine are obtained. Yield: 92% M.p. 148° C(decomp.)

Infrared absorption spectrum $\nu_{max}^{nujol}$ cm$^{-1}$: 3320, 3080, 1620

Nuclear magnetic resonance spectrum

δ(in CF$_3$COOD-D$_2$O): 4.89(1H, s), 5.08(1H, s)

B. A 300 ml beaker is used as an electrolysis cell, and said cell is divided into two compartments(i.e., the anode and cathode chambers) by the porous cup of an unglazed ceramic. The cathode chamber is charged with 100 ml of an aqueous methanol solution containing 2.24 g of threo-γ,γ,γ-trichlorothreonine and 3.2 g of tetraethylammonium chloride. On the other hand, the anode chamber is charged with an aqueous methanol solution containing tetraethylammonium chloride(0.1 g/ml). The level of the electrolytes are made equal in the two chambers. Further, platinum wire is used as the anode, and a mercury pool as the cathode. Electrolysis is carried at 15° to 20° C and at a current density of 50 mA/cm² for 1 hour. After the reaction is completed, the catholyte solution is evaporated under reduced pressure to remove solvent. The residue is dissolved in 50 ml of water, and the aqueous solution is passed through a column(3.5 cm × 50 cm) charged with a cation exchange resin(H+ form) (manufactured by Rohm & Haas Company under the trade name "Amberlite IR-120"). The column is washed with water until the pH of the effluent becomes neutral. Then, the column is eluted with 5% aqueous ammonia. The eluate is concentrated under reduced pressure. The residue thus obtained is dissolved in 30 ml of water, and the aqueous solution is passed through a column (2 cm × 30 cm) charged with a cation exchange resin(H+ form) (manufactured by Rohm & Hass Company under trade name "Amberlite IRC-50"). The effluent is concentrated under reduced pressure, whereby 1.20 g of threo-threonine are obtained. Yield: 75% M.p. 184° - 190° C(decomp.)

What we claim is:

1. Trans-4-alkoxycarbonyl (or aralkyloxycarbonyl)-5-trihalogenomethyl-2-oxazoline of the formula:

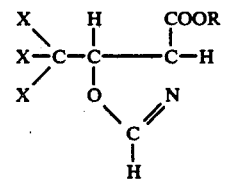

wherein R is methyl, ethyl, propyl, isopropyl, butyl, isobutyl, tert-butyl, amyl, isoamyl, or benzyl, and X chlorine or bromine.

* * * * *